United States Patent

Wagner et al.

[11] Patent Number: 5,834,500
[45] Date of Patent: Nov. 10, 1998

[54] SULFUR-CONTAINING HETEROCYCLIC BRADYKININ ANTAGONISTS, PROCESS FOR THEIR PREPARATION, AND THEIR USE

[75] Inventors: Adalbert Wagner, Gersthofen; Holger Heitsch, Mainz-Kastel; Gerhard Nölken, Sulzbach; Klaus Wirth, Kriftel; Bernward Schölkens, Kelkheim, all of Germany

[73] Assignee: Hoechst Aktiengesellschaft, Germany

[21] Appl. No.: 858,077

[22] Filed: May 16, 1997

[30] Foreign Application Priority Data

May 22, 1996 [DE] Germany .................. 196 20 508 U

[51] Int. Cl.$^6$ .................. A61K 31/425; C07D 277/64
[52] U.S. Cl. .................. 514/367; 548/163; 548/164; 548/161; 548/169; 548/178
[58] Field of Search .................. 514/367; 548/161, 548/163, 164, 169, 178

[56] References Cited

U.S. PATENT DOCUMENTS

| | | | |
|---|---|---|---|
| 4,863,923 | 9/1989 | Ho et al. | 514/443 |
| 5,126,165 | 6/1992 | Akihama et al. | 427/53.1 |
| 5,212,182 | 5/1993 | Musser et al. | 514/314 |
| 5,438,064 | 8/1995 | Mobilio et al. | 514/313 |
| 5,491,156 | 2/1996 | Streeting et al. | 514/367 |

FOREIGN PATENT DOCUMENTS

| | | |
|---|---|---|
| 0 299 457 | 1/1989 | European Pat. Off. |
| 0 596 406 | 5/1994 | European Pat. Off. |
| 0 622 361 A1 | 11/1994 | European Pat. Off. |
| 0 707 852 | 4/1996 | European Pat. Off. |
| 95/06469 | 3/1995 | WIPO. |
| 96/12491 | 5/1996 | WIPO. |
| 96/13485 | 5/1996 | WIPO. |

OTHER PUBLICATIONS

Brockmann et al., Chem. Ber., vol. 103: 708–717 (1970).
König et al., Chem. Ber., vol. 103: 2052–2061 (1970).
Handbook of Exp. Pharmacol. 25: 53–55 (1970), Springer Verlag.
Wirth et al., Hoe 140 a new potent and long acting bradykinin–antagonist: in vivo studies, Br. J Pharmacol., vol. 102: 774–777 (1991).
Innis et al., [$^3$H] Bradykinin receptor binding in mammalian tissue membranes, Proc. Natl. Acad. Sci. USA, vol. 78: 2630–2634 (1981).

*Primary Examiner*—Johann Richter
*Assistant Examiner*—Laura R.C. Lutz
*Attorney, Agent, or Firm*—Finnegan, Henderson, Farabow, Garrett & Dunner, L.L.P.

[57] ABSTRACT

Sulfur-containing heterocyclic bradykinin antagonists, process for their preparation, and their use Compounds of the formula (I)

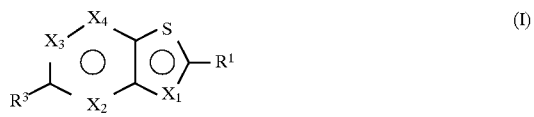

in which one of the radicals $X_1$, $X_2$ or $X_3$ is C—O—$R^2$ and the other $X_1$, $X_2$, and $X_3$, in each case, and $X_4$, are then, identically or differently, N or $CR^1$; $R^1$ and $R^3$ are, identically or differently, H, halogen, ($C_1$–$C_6$)-alkyl, O—$R^6$, S—$R^6$, NH$R^6$, ($C_6$–$C_{12}$)-aryl, ($C_6$–$C_{12}$)-aryl-($C_1$–$C_3$)-alkyl, C(O)—O$R^6$, C(O)—H, ($C_2$–$C_5$)-alkenyl, NO$_2$, SO$_3R^7$, CN or C(O)—NH$R^8$, where alkyl, aryl and alkenyl can optionally be substituted.

22 Claims, No Drawings

SULFUR-CONTAINING HETEROCYCLIC BRADYKININ ANTAGONISTS, PROCESS FOR THEIR PREPARATION, AND THEIR USE

EP-A 622 361, U.S. Pat. No. 5,212,182, U.S. Pat. No. 5,126,165 and U.S. Pat. No. 5,438,064 disclose O- and N-substituted quinolines and their use as bradykinin receptor antagonists.

The present invention relates to sulfur-containing heterocyclic compounds which exhibit improved pharmacokinetics.

The compounds are described by formula (I)

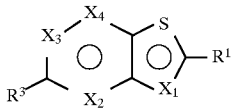

in which the symbols have the following meanings:
a) one of the radicals $X_1$, $X_2$ or $X_3$ is C—O—$R^2$, and the other $X_1$, $X_2$, and $X_3$, in each case, and $X_4$, are then, identically or differently,
  (1) N
  (2) $CR^1$;
b) $R^1$ and $R^3$ are, identically or differently,
  (1) H
  (2) halogen
  (3) $(C_1-C_6)$-alkyl
  (4) O—$R^6$
  (5) S—$R^6$
  (6) $NHR^6$
  (7) $(C_6-C_{12})$-aryl
  (8) $(C_6-C_{12})$-aryl-$(C_1-C_3)$-alkyl
  (9) C(O)—$OR^6$
  (10) C(O)—H
  (11) $(C_2-C_5)$-alkenyl
  (12) $NO_2$
  (13) $SO_3R^7$
  (14) CN
  (15) C(O)—$NHR^8$
  where (3), (7), (8) and (11) can optionally be substituted by one or more groups such as C(O)—(O)$_O$—$(C_1-C_5)$-alkyl, $OR^6$, $SR^7$, $NO_2$, CN, $NHR^8$ or halogen;
c) $R^2$ is a radical of the formula

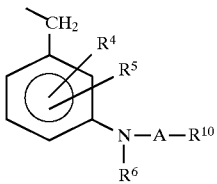

d) $R^4$ and $R^5$ are, identically or differently,
  (1) H
  (2) halogen
  (3) $OR^6$
  (4) $SR^6$
  (5) CN
  (6) $(C_1-C_5)$-alkyl;
e) $R^6$, $R^7$ and $R^8$ are, identically or differently,
  (1) H
  (2) $(C_1-C_5)$-alkyl
  (3) $(C_3-C_5)$-alkenyl
  (4) $(C_6-C_{12})$-aryl-$(C_1-C_3)$-alkyl;
  (5) $(C_3-C_{10})$-cycloalkyl,
  (6) $(C_3-C_{10})$-cycloalkyl-$(C_1-C_3)$-alkyl;
  (7) C(O)—(O)$_O$—$(C_1-C_5)$-alkyl,
  (8) C(O)—(NH)$_O$—$(C_1-C_5)$-alkyl;
f) A is an aminocarboxylic acid, for example methionine, alanine, phenylalanine, 2-chlorophenylalanine, 3-chlorophenylalanine, 4-chlorophenylalanine, 2-fluorophenylalanine, 3-fluorophenylalanine, 4-flourophenylalanine, tyrosine, O-methyltyrosine, β-(2-thienyl)alanine, glycine, cyclohexylalanine, leucine, isoleucine, valine, norleucine, phenylglycine, serine, cysteine, aminopropionic acid or aminobutyric acid;
g) $R^9$ is
  (1) H
  (2) C(O)—(O)$_O$—$(C_1-C_5)$-alkyl
  (3) C(O)—(O)$_O$—$(C_1-C_3)$-alkyl-$(C_6-C_{10})$aryl;
h) $R^{10}$ is
  (1) —C(O)—D—E
  (2) —C(S)—D—E
  (3) —$SO_2$—D—E
  (4) hydrogen;
i) D is
  (1) $(C_2-C_5)$-alkenediyl
  (2) $(C_1-C_8)$-alkanediyl
  (3) —$(CH_2)_n$—$Y_O$—$(CH_2)_m$—
  (4) $(C_3-C_{10})$-cycloalkanediyl
  (5) $(C_3-C_{10})$-cycloalkyl-$(C_1-C_3)$-alkanediyl
  (6) $(C_3-C_{10})$-cycloalkenediyl
  (7) $(C_3-C_{10})$-cycloalkenyl-$(C_1-C_3)$-alkanediyl
  where (1)-(7) can optionally be substituted by one or more groups such as $OR^6$, $NO_2$, CN, $CO_2R^7$, $NR^8R^9$, $SO_2R^6$, $SO_2NR^8R^9$, $SO_3R^7$ or C(O)—$NR^8R^9$;
j) E is
  (1) H
  (2) $(C_6-C_{10})$-aryl,
  (3) $(C_1-C_9)$-heteroaryl,
  where (2) and (3) can optionally be substituted by one or more groups such as $NR^8R^9$, CN, $CO_2R^6$, $SO_3R^7$, $NO_2$, $SO_2NR^8R^9$, $SO_2R^6$, O—$(C_1-C_5)$-alkyl, S—$(C_1-C_5)$-alkyl, $(C_1-C_5)$-alkyl or $(C_2-C_5)$-alkenyl, where O—$(C_1-C_5)$-alkyl and $(C_1-C_5)$-alkyl can optionally be partially or completely substituted by halogen;
k) Y is
  (1) O
  (2) S
  (3) $NR^8$;
l) n and m are, identically or differently, a number 0–6;
m) o is 0 or 1;
and the physiologically tolerated salts thereof.

Alkyl and alkenyl can be straight-chain or branched. The same applies, in a corresponding manner, to the radicals, such as alkoxy, which are derived from them.

Alkenyl is monounsaturated or polyunsaturated compounds, such as 1,4-butadienyl, 8,11-heptadienyl, 8,11, 14-heptatrienyl, and butenyl. The same applies, in a corresponding manner, to cycloalkenyl.

Cycloalkyl is monocyclic or bicyclic compounds, such as cyclopropyl, cyclopentyl, cyclohexyl and bicyclononyl. The same applies, in a corresponding manner, to cycloalkenyl.

$(C_6-C_{12})$-aryl is, for example, phenyl, naphthyl or biphenyl, preferably phenyl. The same also applies, in a corresponding manner, to radicals, such as aralkyl, which are derived from them.

Halogen (Hal) is fluorine, chlorine, bromine or iodine, preferably chlorine or fluorine.

($C_1$–$C_9$)-Heteroaryl is understood as being radicals which are derived from phenyl or naphthyl and in which one or more CH groups are replaced by N and/or in which at least two adjacent CH groups are replaced with S, NH or O (with the formation of a five-membered aromatic ring). In addition, one or both atoms of the fusion site of bicyclic radicals (such as in indolizinyl) can also be N atoms.

Heteroaryl is regarded, in particular, as being furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl, benzopyranonyl, coumarinyl, pyranonyl and furandionyl.

Physiologically tolerated salts of compounds of the formula (I) are understood as being both their organic salts and their inorganic salts, as described in Remington's Pharmaceutical Sciences (A. R. Gennard, Editor, Mack Publishing Co., Easton, Pa. 17th Edition, page 1418 (1985)). Owing to their physical and chemical stability, and their solubility, sodium, potassium, calcium and ammonium salts, inter alia, are preferred for acidic groups; salts of hydrochloric acid, sulfuric acid or phosphoric acid, or of carboxylic acids or sulfonic acids, inter alia, such as acetic acid, citric acid, benzoic acid, maleic acid, fumaric acid, tartaric acid and p-toluenesulfonic acid, are preferred for basic groups.

Compounds of the formula (I) are preferred in which
a) $R^1$ and $R^3$ are, identically or differently,
  (1) H
  (2) ($C_1$–$C_6$)-alkyl
  (3) O—$R^6$
  (4) S—$R^6$
  (5) $NHR^6$
  (6) ($C_2$–$C_5$)-alkenyl
  (7) C(O)—$OR^6$
  (8) C(O)—H
  (9) $NO_2$
  (10) CN
  (11) C(O)—$NHR^8$
  where (2) and (6) can optionally be substituted by one or more groups, such as halogen, $CO_2R^6$, or $NHR^8$;
b) $R^6$, $R^7$ and $R^8$ are, identically or differently,
  (1) H
  (2) ($C_1$–$C_5$)-alkyl
  (3) ($C_6$–$C_{10}$)-aryl-($C_1$–$C_3$)-alkyl;
and the remaining radicals and variables are defined as above.

Compounds of the formula (I) are particularly preferred in which
a) $R^1$ and $R^3$ are, identically or differently,
  (1) H
  (2) ($C_1$–$C_4$)-alkyl
  (3) NH—($C_1$–$C_5$)alkyl
  (4) O—($C_1$–$C_5$)alkyl
  (5) S—($C_1$–$C_5$)-alkyl
  (6) C(O)—H
  (7) $CO_2R^6$
  (8) ($C_2$–$C_3$)-alkenyl
  where (2)-(5) and (8) can be substituted by one or more radicals, such as halogen, $CO_2R^6$ or $NHR^8$;
b) A is leucine, isoleucine, valine, alanine, methionine, glycine, serine, aminopropionic acid or aminobutyric acid;
and the remaining radicals and variables are defined as above.

The invention furthermore relates to a process for preparing compounds of the formula (I), which comprises $a_1$) (1) firstly acylating, at temperatures of between 0° and 20° C., a compound of the formula (III)

in which $R^3$, $X_2$, $X_3$ and $X_4$ are defined as above in formula (I), with activated carboxylic acid derivatives, preferably their acyl chlorides, using an auxiliary base, preferably triethylamine or diisopropylethylamine, (2) heating the resulting compound of the formula (IV)

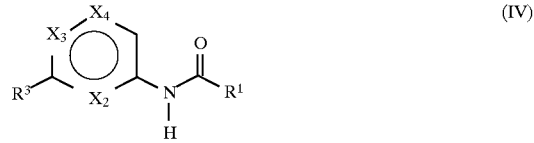

to boiling with Laweson's reagent or preferably $P_2S_{10}$ in butyl acetate or other inert high-boiling point solvents, and thereby obtaining a compound of the formula (V),

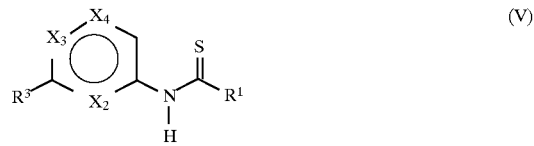

in which $R^1$, $R^3$, $X_2$, $X_3$ and $X_4$ in formulae IV and V are defined as above in formula (I), and where, when $X_2$ or $X_3$ is C—O—$R^2$, $R^2$ is $R^{2'}$=H or ($C_1$–$C_5$)-alkyl, preferably methyl or ethyl, (3) reacting the resulting compound (V), by means of free-radical cyclization, with free-radical-generating reagents, preferably $K_3Fe(CN)_6$ or $Br_2$ in inert solvents, preferably $H_2O$, at temperatures of between 80° and 110° C., and thereby obtaining a compound of formula (VI)

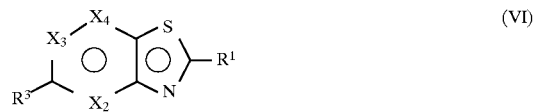

in which the radicals $R^1$, $R^3$, $X_2$, $X_3$ and $X_4$ are defined as above in formula (I), and where, when $X_2$ or $X_3$ is C—O—$R^2$, $R^2$ is $R^{2'}$=H or ($C_1$–$C_5$)-alkyl, preferably methyl or ethyl, (4) converting a compound of the formula (VI), in which $X_2$ or $X_3$ is C—O—$R^2$ and is defined as under (3), by means of ether-cleaving reagents, preferably $BBr_3$, HI/red phosphorus, HBr or HBr/$CH_3CO_2H$, in inert solvents or without solvent, at temperatures of between 0° C. and the boiling point, into compounds of the formula (VI) in which $X^2$ or $X^3$ is $COR^2$ and $R^2$=$R^{2'}$=hydrogen;

or $a_2$) (1) converting a compound of the formula (VII)

in which $R^3$, $X_3$, and $X_4$ are defined as above in formula (I) and M is potassium, sodium or cesium, by successive treatment with $CO_2$ and then $NH_3$ under elevated pressure and temperatures, preferably 100 atm and 200° C., into a compound of the formula (VIII),

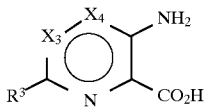
(VIII)

in which $R^3$, $X_3$ and $X_4$ are defined as above in formula (I), (2) converting a compound of the formula (VIII), by diazotization and subsequent treatment with $HS\text{—}CHR^1\text{—}CO_2H$, into a compound of the formula (IX)

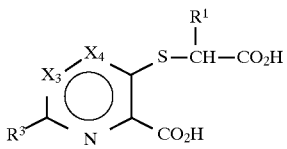
(IX)

in which $R^1$, $R^3$, $X_3$ and $X_4$ are defined as above in formula (I), (3) converting a compound of the formula (IX), by means of cyclization with simultaneous decarboxylation and water elimination, in inert solvents, preferably $H_2O$, or without solvent, preferably at temperatures of ~100° C., into a compound of the formula (X),

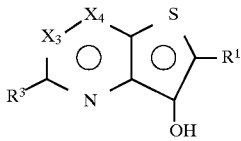
(X)

in which $R^1$, $R^3$, $X_3$ and $X_4$ are defined as above in formula (I);

b) deprotonating a compound of the formulae (VI) or (X)

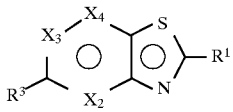
(VI)

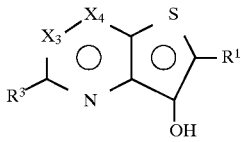
(X)

in which $X_2$, $X_3$, $X_4$, $R^1$ and $R^3$ are defined as above in formula (I), in the case of compounds of the formula (VI), $X_2$ or $X_3$ is C—O—H, with $Cs_2CO_3$ or $K_2CO_3$ in an inert solvent, preferably DMF or N-methylpyrrolidine, and reacting it, at room temperature, with a compound of the formula (XI)

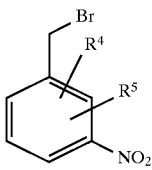
(XI)

in which $R^4$ and $R^5$ are defined as above in formula (I);

c) reducing the resulting compounds of the formulae (XII) or (XII')

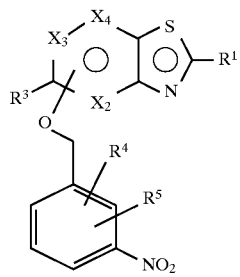
(XII)

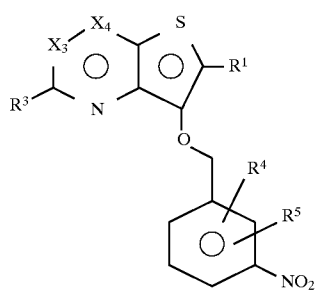
(XII')

in which $R^1$, $R^3$, $R^4$, $R^5$, $X_2$, $X_3$ and $X_4$ are defined as above in formula (I), with the aid of transition metal halides, preferably $SnCl_2$ or $FeCl_3$, to form a compound of the formulae (XIII) or (XIII'),

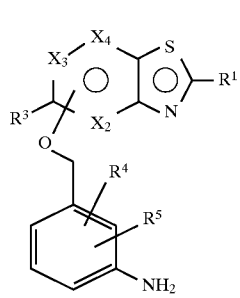
(XIII)

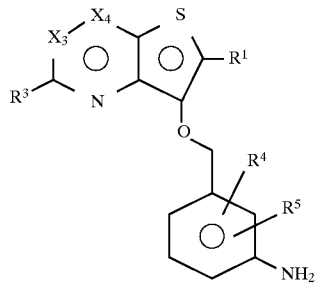
(XIII')

in which $R^1$, $R^3$, $R^4$, $R^5$, $X_2$, $X_3$ and $X_4$ are defined as above in formula (I);

d) reacting a compound of the formulae (XIII) or (XIII') with activated, suitably protected, aminocarboxylic acid derivatives of A (A-Prot), preferably the acyl chlorides of the phthaloyl-protected aminocarboxylic acid derivatives of A, in inert solvents such as NMP, where appropriate by adding DMAP, and thereby obtaining a compound of the formulae (XIV) or (XIV'),

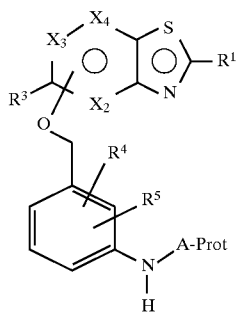
(XIV)

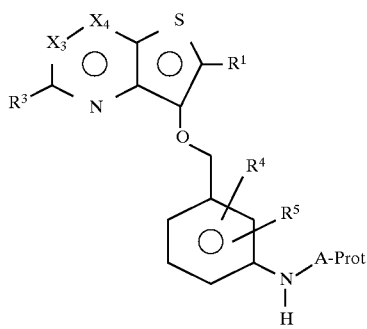
(XIV')

in which A, $R^1$, $R^3$, $R^4$, $R^5$, $X_2$, $X_3$ and $X_4$ are defined as above in formula (I), $R^6$ is hydrogen, and Prot is an amino protecting group as described in T. W. Greene "Protective Groups in Organic Synthesis", John Wiley Publishers, 2nd edition, 1991, with both protons of the amino protecting group being protected, for example benzyl, paramethoxybenzyl or phthaloyl;

e) reacting a compound of the formulae (XIV) or (XIV'), after alkali metal hydrides, alkali metal carbonates or alcoholates, in inert solvents, preferably DMF or NMP, have acted on it, with $R^6X$, in which $R^6$ is other than hydrogen as defined as above in formula (I) and X is a leaving group, for example halogen, mesylate or tosylate, thereby obtaining a compound of the formulae (XV) or (XV'),

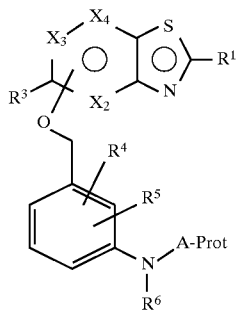
(XV)

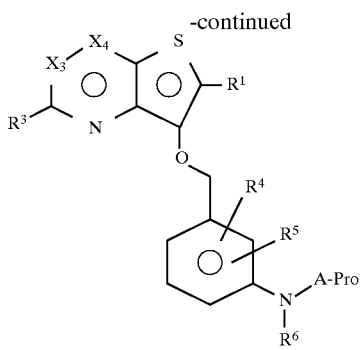
(XV')

in which A, $R^1$, $R^3$, $R^4$, $R^5$, $R^6$, $X_2$, $X_3$ and $X_4$ are defined as above in formula (I), $R^6$ is other than hydrogen, and Prot is defined as above in formula (XIV);

f) for the purpose of removing the protecting group (Prot.) from the compound of the formulae (XV) or (XV'), the latter is preferably reacted with hydrazine, in the case of the phthaloyl group, in alcohols as solvents, at temperatures of between room temperature and the boiling point, preferably at room temperature, thereby affording a compound of the formulae (XVI) or (XVI'),

(XVI)

(XVI')

in which A, $R^1$, $R^3$, $R^4$, $R^5$, $R^6$, $X_2$, $X_3$ and $X_4$ are defined as above in formula (I) and Prot is defined as above in formula (XIV);

g$_1$) reacting a compound of the formulae (XVI) or (XVI') with activated acid derivatives of the formulae (XVII), (XVIII) or (XIX)

$$E-D-C(O)-OH \quad \text{(XVII)}$$
$$E-D-C(S)-OH \quad \text{(XVIII)}$$

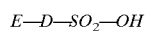  (XIX)

in which D and E are defined as above in formula (I), preferably their acid chlorides or anhydrides, or acids of the formulae (XVII), (XVIII) or (XIX) which are activated with reagents as used in peptide synthesis, or g$_2$) reacting a compound of the formulae (XVI) or (XVI') with an amine or an alcohol of the formula (XX)

  (XX)

in which E and D are defined as above and Z is OH or NH$_2$, preferably at temperatures of between 0° C. and room temperature, in inert solvents, preferably dichloromethane or dimethoxyethane, with, however, the compounds of the formulae (XVI), (XVI') or (XX) first being allowed to react with a doubly activated carbonyl compound for the purpose of forming the urea group or urethane group, for example with carbodiimides, phosgene or chlorocarbonates, preferably phosgene and carbonyidiimidazole, or g$_3$) reacting a compound of the formulae (XVI) or (XVI') with an appropriate isocyanate or isothiocyanate, preferably at temperatures of between 0° C. and room temperature, in inert solvents, preferably dichloromethane or dimethoxyethane, and h) where appropriate, using known methods to convert the resulting compound of the formula (I) into its physiologically tolerated salts.

Chlorine is replaced with alkoxy or the corresponding S-alkylene by reacting with the corresponding alcoholates or thiolates, preferably their alkali metal or alkaline earth metal salts, in inert solvents, preferably DMF, NMP or the corresponding alcohol, at temperatures of between 0° C. and 60° C., preferably between 0° C. and room temperature.

Chlorine is replaced with cyano by the action of cyanides, preferably the copper cyanides, in inert high-boiling point solvents, such as DMF or NMP, at their boiling points.

Conversion to the bromoethyl compound is effected by reacting the corresponding methyl derivative with N-bromosuccinimide, dibromohydantoin or bromine in inert solvents, preferably bromobenzene or cyclohexane, at temperatures of from 60° C. up to the boiling point.

Aminocarboxylic acid includes methionine, alanine, phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, O-methyltyrosine, β-(2-thienyl)alanine, glycine, cyclohexylalanine, leucine, isoleucine, valine, norleucine, phenylglycine, serine, cysteine, aminopropionic acid and aminobutyric acid. It is well understood in the art that such aminocarboxylic acids can be substituted at either their amino terminus, their carboxy terminus, or both their amino and carboxy terminuses. Thus, it is understood that the substituent A in formula (I) is an aminocarboxylic acid having substituents at both its amino and carboxy terminuses, $R^{10}$ being at the amino terminus, while in the process scheme, step e, A is an aminocarboxylic acid having a protecting group at the amino terminus, and in step f, A is an aminocarboxylic acid having an unsubstituted amino terminus.

All the possible activating reagents which are used in peptide synthesis, see, for example, Houben-Weyl, Methoden der Organischen Chemie [Methods of Organic Chemistry], Volume 15/2, Georg Thieme Verlag, Stuttgart 1974, in particular, however, carbodiimides such as N,N'-dicyclohexylcarbodiimide, N,N'-diisopropylcarbodiimide or N-ethyl-N'-(3-dimethylaminopropyl)carbodiimide, can be used as the coupling reagent. In this context, the coupling can take place directly, by adding carboxylic acid derivative with the activating reagent and, where appropriate, an additive such as 1-hydroxybenzotriazole (HOBt) (W. König, R. Geiger, Chem. Ber. 103, 708 (1970)) or 3-hydroxy-4-oxo-3,4-dihydrobenzotriazine (HOObt) (W. König, R.Geiger, Chem. Ber. 103, 2054 (1970)), or else the carboxylic acid derivative can be preactivated separately as a symmetric anhydride or HOBt or HOObt ester and the solution of the activated species in a suitable solvent can be added to the amine.

The coupling or activation of the amino acid derivatives using one of the above-mentioned activating reagents can be carried out in dimethylformamide, N-methylpyrrolidone or methylene chloride, or a mixture of the said solvents.

Protecting groups which protect both protons of the amino group, for example two benzyl groups, can also be used in place of the phthaloyl group.

Individually or in combination, the novel compounds possess a bradykinin-antagonistic effect which can be tested in various models (see Handbook of Exp. Pharmacol. Vol. 25, Springer Verlag, 1970, pp. 53–55), for example on the isolated rat uterus, on the guinea pig ileum, on the rabbit jugular vein or on the isolated guinea pig pulmonary artery. The effects of the compounds of the formula (I) on bradykinin-induced bronchoconstriction and carrageenin-induced paw oedema can be determined in analogy with Br. J. Pharmacol. 102, 774–777 (1991).

The method of measuring binding to the bradykinin $B_2$ receptor of guinea pig ileum is described below (R. B. Innis et al., Proc. Natl. Acad. Sci. USA; 17 (1981) 2630):

1. Ligand: $^3$H-BRADYKININ (from NEN Du Pont)
2. Buffer mixtures:
   a) TES buffer:
      25 mM TES (SIGMA, Cat. No.: T-4152)
      1 mM 1,10-phenanthroline (SIGMA; Cat. No.: P-9375)
   b) Incubation buffer:
      25 mM TES (SIGMA; Cat. No.: T-4152)
      1 mM 1,10-phenanthroline (SIGMA; Cat. No.: P-9375)
      0.1% albumin, bovine (SIGMA; Cat. No.: A-7906)
      140 μg/ml bacitracin (SIGMA; Cat. No.: B-0125)
      1 mM dithiothreitol (SIGMA; Cat. No.: D-0632)
      1 μM captopril→ 1-[(2S)-3-Mercapto-2-methylpropionyl]-L-proline Both buffers are adjusted to pH 6.8 with 5 molar NaOH.

3. Membrane preparation:
   Guinea pig ilea are roughly freed of intestinal contents by carefully smoothing them out and are cleansed in 0.9% NaCl solution. The approx. 2 cm-long ilea pieces are transferred into ice-cold TES buffer (approx. 1 g/10 ml) and homogenized with an Ultraturrax for approx. 30 sec. in an ice bath. The homogenate is then filtered through 3 layers of gauze and the filtrate is centrifuged at 50,000 g for 10 minutes. The supernatant is discarded and the pellet is rehomogenized in the same volume of TES buffer and centrifuged once again at 50,000 g for 10 minutes. The pellet is rehomogenized in incubation buffer (approx. 1 g/5 ml) and frozen down at −70° C., in 2 ml aliquots, in cryotubes.

The protein concentration of the finished membrane suspension is determined by the LOWRY method and should be approx. 15 μg/100 μl.

4. Binding test:
   All the incubations are carried out, at room temperature for 60 minutes, in a 200 μl volume on microtiter plates (96×300 μl). All the mixtures are in incubation buffer. For this, 50 µl of the radioligand, 50 µl of the preparation to be tested and 100 µl of the membrane suspension are pipetted consecutively into the wells of the microtiter plate.

a) Saturation experiments (hot saturation):

Preparation of the $^3$H-bradykinin solution: The concentrations 0.05, 0.1, 0.2, 0.4, 0.6, 0.8, 1.0, 1.5, 2.0, 2.5 and 3.0 nmol/l, corresponding to 0.05 to 3.0 pmol/ml, are employed for the saturation experiments. After the appropriate dilutions have been prepared, 50 µl are in each case introduced per sample.

Nonspecific binding: The nonspecific binding has to be determined for each concentration of the radioactive ligand. This can be done by adding a high concentration (1–100 µmol) of the unlabeled ligand or of other antagonists or agonists of the bradykinin receptor. HOE 140 (10 µmol/l) is used in this test. For this, 1.862 mg are dissolved in 1 ml of dimethyl sulfoxide (DMSO); the solution is then diluted 1:25 with incubation buffer and 50 µl of the resulting solution are added to the samples in the microtiter plate. The reaction is started by adding 100 µl of the membrane suspension.

b) Competition experiments (IC$_{50}$):

A fixed quantity of the radioactive ligand (from 0.25 to 0.3 nmol/l $^3$H-bradykinin) and different concentrations of the unlabeled agonists or antagonists are employed for this purpose.

50 µl of the preparations or the standards to be tested, are added, in concentrations of from $10^{-5}$ to $10^{-10}$ mol/l, to in each case 50 µl of the $^3$H-bradykinin solution and the reaction is started by adding 100 µl of membrane suspension. In this test, too, determinations are carried out in triplicate and three samples are incubated for determining the nonspecific binding using 10 µmol/l HOE 140.

As a rule, the preparations which are to be tested for competition are dissolved, at a concentration of 1 mmol/l, in dimethyl sulfoxide (DMSO) and subsequently subjected to further dilution with DMSO. This solution is then diluted 1:25 with incubation buffer. After the incubation, the samples are filtered off, in a Skatron cell harvester, on a Whatmann GF/B filter paper strip which has previously been moistened with 0.1% PEI (polyethyleneimine), after which each sample is then washed with 10 ml of ice-cold TES buffer. The filters, which are still moist, are punched out into mini scintillation vials, which are filled with 3 ml of scintillator. After having been left to soak for approx. 12 hours, the samples are shaken up briefly and measured in a beta counter.

c) Screening:

In general, only 1–2 concentrations of the test preparation ($10^{-5}$ and $10^{-6}$ mol/l) are employed in the primary screening. If 50% more of the radioligand can be demonstrated to be displaced in the presence of the highest concentration, a complete analysis (competition experiment) is performed using at least 8 concentrations.

4. Evaluation:

The evaluation is effected by means of the LIGAND program package (McPherrson, Minson & Rodbard, Marketing: Elsevier-BIOSOFT), which performs the necessary calculations for determining IC$_{50}$ and K$_i$ values. This program also performs graphic depictions of the saturation and displacement curves and also SCATCHARD plots, HILL plots or HOFSTEE plots.

Antagonistic effects on the bradykinin-induced contraction of guinea pig ileum are determined in accordance with the following protocol:

Guinea pigs of approx. 300 g in weight (Morioth strain,__) are killed by a blow to the neck and exsanguinated. An ileum length of approx. 20 cm is dissected out and rinsed thoroughly with Tyrode solution (Record syringe) so as to free it from intestinal content. It is then divided into segments of 1.5 cm in length. These segments are fastened in 10 ml-capacity organ baths, which are filled with Tyrode solution, and connected to strain gauges (measurement of isometric contraction). The initial load is 1 g. The Tyrode solution is warmed to 37° C. in a water bath and compressed air is bubbled through it.

The experiment is started after an interval of 30 min.

After recording the biological zero line, bradykinin is added to a final concentration of $4\times10^{-8}$ mol/l per organ bath and the concentration is recorded. After that, rinsing with Tyrode solution takes place for 3 min. and bradykinin is added once again after a rest period of 20 min. The contraction maximum is reached (control). Rinsing takes place once again followed by a rest period. The bradykinin antagonist is now added (period allowed for exerting an effect, 10 min.). After that, bradykinin is added once again and the contraction which now takes place is compared with the control. The experiment is plotted on a pen recorder.

| Tyrode solution (mM): | |
|---|---|
| NaCl | 137 |
| glucose | 5.05 |
| KCl | 2.68 |
| NaHCO$_3$ | 11.9 |
| NaH$_2$PO$_4$ | 0.47 |
| MgCl$_2$ × 2H$_2$O | 0.49 |
| CaCl$_2$ × 2H$_2$O | 0.68 |

Amplifier: TF6 V3 from Fleck, Mainz
Pen recorder: Goerz Metrawatt SE 460, BBC
Bradykinin: from Bachem For testing the novel compounds on the isolated pulmonary artery, guinea pigs (Dunkin Hartley) having a weight of 400–450 g are killed by a blow to the neck.

The thorax is opened and the pulmonary artery is carefully dissected out. The surrounding tissue is carefully removed and the pulmonary artery is cut open spirally at an angle of 45°.

The blood vessel strip, which is 2.5 cm long and 3–4 mm wide, is fastened in a 10 ml-capacity organ bath which is filled with Ringer solution.

| Composition of the solution in mmol/l | |
|---|---|
| NaCl | 154 |
| KCl | 5.6 |
| CaCl$_2$ | 1.9 |
| NaHCO$_3$ | 2.4 |
| glucose | 5.4 |

95% O$_2$ and 5% CO$_2$ is bubbled through the solution, which is warmed to 37° C. The pH is 7.4 and the initial load on the vessel strip is 1.0 g.

The isotonic contraction changes are detected with a lever attachment and a high frequency modem (distance measuring device) from Hugo Sachs and registered on a potentiometric recorder (BEC, Goerz Metrawatt SE 460).

The experiment is started after 1 hour of equilibration. Once the maximum sensitivity of the vessel strips to $2\times10^{-7}$ mol/l bradykinin has been reached—bradykinin causes the vessel strips to contract—the test compounds, at doses of $5\times10^{-8}$–$1\times10^{-5}$ mol/l, are allowed to exert their effect for 10 minutes in each case and, after bradykinin has been added once again, the decrease in the effect of bradykinin is compared with the control.

Description of the method for determining the effect of the compounds of the formula (I) on isolated rabbit jugular vein.

Male rabbits (white New Zealand rabbits, breeder: M öllegaard, Denmark, 2.5–3.0 kg) are killed by injecting an overdose of Na pentobarbital (1 ml of Narcoren®+0.5 ml heparin). The two jugular veins are dissected out and cut open spirally, and pieces of approx. 1.5 cm in length are suspended in buffered organ baths (Krebs-Henseleit buffer) at an initial tension of 0.5 g. After a rest period of 30 min, contractions, which serve as the starting value, are elicited by adding bradykinin ($10^{-7}$M). Test substances are now added at a concentration of $10^{-5}$M. The inhibition values shown are mean values (n=6). The values given for the 15 min. time point indicate the inhibition of the bradykinin-induced contraction while the test substances are still present in the bath liquid after a 15-minute incubation. After that, the bradykinin contraction is terminated by rinsing with buffer solution alone. Renewed stimulation with bradykinin took place at each subsequently listed time point (in the absence of the test substance in the bath liquid) and the bath liquid was replaced with buffer solution alone in order to terminate the contraction.

Using the above-described methods, the antagonistic effect expressed as $IC_{50}$-value of Examples 3, 6, 11, 12, 23 and 37, without there being any restriction to these examples, on the guinea pig $B_2$ receptor was found to be less than $1 \times 10^{-7}$M and on the guinea pig pulmonary artery was found to be less than $1 \times 10^{-6}$M.

For the oral use form, or for application to the mucous membranes, the active compounds are mixed with the additives which are customary for this purpose, such as carrier substances, stabilizers or inert diluents, and brought, using customary methods, into suitable forms for administration, such as tablets, coated tablets, hard gelatin capsules, aqueous, alcoholic or oily suspensions, or aqueous, alcoholic or oily solutions. Examples of inert excipients which may be used are gum arabic, magnesium hydroxide, magnesium carbonate, potassium phosphate, lactose, glucose, magnesium stearyl fumarate or starch, in particular corn starch. In this context, the preparation can be effected either as a dry granulate or as a wet granulate. Examples of suitable oily carrier substances or solvents are vegetable or animal oils, such as sunflower oil and cod liver oil.

A preparation for topical use can be present as an aqueous or oily solution, lotion, emulsion or jelly, ointment or greasy ointment, or, if possible, be present in spray form, with it being possible, where appropriate, to improve adherence by adding a polymer.

For an intranasal use form, the compounds are mixed with the additives which are customary for this purpose, such as stabilizers or inert diluents, and brought, using customary methods, into suitable forms for administration, such as aqueous, alcoholic or oily suspensions, or aqueous, alcoholic or oily solutions. Chelating agents, ethylenediamine-N,N,N',N'-tetraacetic acid, citric acid or tartaric acid, or their salts, can be added to aqueous intranasal preparations. The nasal solutions can be administered by means of a dosing atomizer or as nasal drops containing a viscosity-increasing constituent, or nasal gels or nasal creams.

The described compounds of the formula (I), and their pharmacologically suitable salts, are potent bradykinin antagonists. Their therapeutic benefit therefore lies in the treatment and/or prevention of all pathological conditions which are mediated, evoked or promoted by bradykinin and bradykinin-analogous peptides. This includes, inter alia, allergies, inflammations, autoimmune diseases, shock and pain, and, more specifically, asthma, coughing, bronchitis, rhinitis, chronically obstructive pulmonary diseases, pneumonitis, septic shock, endotoxic shock, anaphylactic shock, disseminating intravascular coagulopathy, arthritis, rheumatism, osteoarthritis, lumbago, inflammation-induced bone resorption, conjunctivitis, iritis, headache, migraine, toothache, backache, cancer-associated pains, postoperative pain, traumas (wounds, burns, etc.), exanthema, erythemas, edemas, eczemas, dermatitis, shingles, herpes, pruritus, psoriasis, lichen, inflammatory intestinal diseases, hepatitis, pancreatitis, gastritis, esophagitis, food allergies, ulcers, irritable bowel, angina, cerebral oedema, low blood pressure, thrombosis, cranial-cerebral and spinal trauma, premature birth, atherosclerosis, ascites in association with malignant growth, tumor metastases, cerebral edema in association with tumors, brain lesion caused by heat, viral diseases and hepatic cirrhosis.

Since it is also known that bradykinin is linked to the release of mediators such as prostaglandins, leukotrienes, tachykinins, histamine and thromboxanes, the compounds of the formula (I) consequently also possess the potential for treating and/or preventing diseases which are elicited by these mediators.

The invention also relates, therefore, to the use of compounds of the formula (I) as medicines and pharmaceutical preparations which comprise these compounds.

Pharmaceutical preparations comprise an effective quantity of the active compound of the formula (I)—either alone or in combination—together with an inorganic or organic pharmaceutically utilizable carrier substance. The active compound can be administered by the enteral, parenteral—such as subcutaneous, i.m. or i.v., sublingual, epicutaneous, nasal, rectal, intravaginal or intrabuccal route, or by means of inhalation. The dose of the active compound administered depends on the homeothermic species and on the body-weight and age, and on the type of administration.

The pharmaceutical preparations of the present invention are produced in solubilizing, mixing, granulating or sugar coating processes which are known per se.

Nebulizers, or compressed-gas packs, employing inert carrier gases, can be used for inhalational applications.

For intravenous, subcutaneous, epicutaneous or intradermal administration, the active compounds, or their physiologically tolerated salts, are brought into solution, suspension or emulsion, if desired together with the pharmaceutically customary auxiliary substances, for example for producing isotonicity or for adjusting the pH, and also solubilizers and emulsifiers, or other auxiliary substances.

If the half-lives of the described medicaments in body fluids are inadequate, it is sensible to use injectable delayed-release preparations. Examples of drug forms which can be used are oily crystal suspensions, microcapsules, rods or implants, with it being possible for the latter to be synthesized from tissue-tolerated polymers, in particular biodegradable polymers, such as polymers which are based on polylactic acid-polyglycolic acid copolymers or human albumin.

Solutions containing 0.01–5 mg/l represent a suitable dose range for topical and inhalational administration forms; a range of 0.01–10 mg/kg is suitable for systemic administration forms. In general, quantities of between 0.1 mg/body and 1000 mg/body may be daily administered. Per body relates to an adult of about 75 kg bodyweight.

List of abbreviations:

| | |
|---|---|
| AIBN | α, α'-azobis(isobutyronitrile) |
| DEI | desorption electron impact |
| DCI | desorption-chemical ionization |
| E | ethyl acetate |
| FAB | fast atom bombardment |
| DME | dimethoxyethane |
| DMF | dimethylformamide |
| DMAP | dimethylaminopyridine |
| NMP | N-methylpyrrolidone |
| H | n-heptane |
| RT | room temperature |
| $CH_2Cl_2$ | dichloromethane |
| h | hours |
| ESI | electron spray ionization |
| T | temperature |

The following examples explain the invention.

EXAMPLE 1

4-[3-(N-(3-Methoxycinnamoylglycyl)-N-methylamino)-2,6-dichlorobenzyloxy]benzothiazole a) 2,6-Dichloro-3-nitrobenzyl bromide A mixture of dibromohydantoin (70 g, 0.24 mol) and AIBN (5 g) was added in portions, at 150° C., to 2,6-dichloro-3-nitrotoluene (100 g, 0.48 mol) in chlorobenzene (400 ml). A mixture of dibromohydantoin (35 g, 0.12 mol) and AIBN (2.5 g) was added once again after 1 h. After a further 1.5 h, the mixture was allowed to cool down and ethyl acetate (500 ml) was added. This mixture was washed once, in each case, with saturated $Na_2SO_3$, $Na_2CO_3$ and NaCl solution, dried ($MgSO_4$) and concentrated, when the title compound resulted as an amorphous powder.

$R_f(E/H\ 1/1) = 0.7\ MS(DEI) = 283(M^+)$ b) 4-(2,6-Dichloro-3-nitrobenzyloxy)benzothiazole The title compound of Example 1a) (6 g, 21.1 mmol) was added, at RT, to 4-hydroxybenzothiazole (Helv. Chim. Acta 25 (1942) 515), (3.3 g, 21.8 mmol) and $K_2CO_3$ (3 g, 21.7 mmol) in DMF (50 ml). After 90 min, the mixture was diluted with ethyl acetate (500 ml) and washed 5 times with 100 ml of $H_2O$ on each occasion; the organic phase was dried ($MgSO_4$) and concentrated. Crystallization from ethyl acetate yields the title compound as an amorphous powder.

$R_f(E/H\ 1/1) = 0.5\ MS(ESI) = 355(M + 1)$ c) 4-(3-Amino-2,6-dichlorobenzyloxy)benzothiazole $SnCl_2 \times H_2O$ (12 g, 53 mmol) was added to the title compound of Example 1b) (3.8 g, 10.7 mmol) in ethyl acetate (50 ml), and the mixture was heated at 70° C. After 1 h, it was allowed to cool down to RT and poured onto ice (approx. 300 g). The pH was now adjusted to 13 by adding 2N NaOH solution and the mixture was extracted 3 times in the cold with 200 ml of ethyl acetate on each occasion. The combined organic extracts were washed once with a saturated solution of $NaHCO_3$ (200 ml), dried ($MgSO_4$) and concentrated; this crude concentrate was used for the next reaction step.

$R_f(E/H\ 1/1) = 0.4\ MS(ESI) = 325(M + 1)$ d) 4-(2,6-Dichloro-3-phthaloylglycylaminobenzyloxy)benzothiazole A mixture of the title compound of Example 1c) (1.2 g, 3.7 mmol), phthaloylglycyl chloride (1.3 g, 7 mmol), DMAP (160 mg, 1.3 mmol) and pyridine (2 ml) in NMP (10 ml) was heated at 50° C. After 2 h, the mixture was allowed to cool down to RT and poured onto $H_2O$ (approx. 200 ml). The resulting precipitate was filtered, washed with $H_2O$ and dried in air.

$R_f(E/H\ 1/1) = 0.3\ MS(FAB) = 512(M + 1)$ e) 4-[3-(N-Phthaloylglycyl-N-methylamino)-2,6-dichlorobenzyloxy]-benzothiazole 50% NaH (170 mg, 3.5 mmol of a 60% suspension in mineral oil) was added, at 0° C. and under argon, to the title compound of Example 1d) (1.8 g, 3.5 mmol) in dry DMF (50 ml). Methyl iodide (500 mg, 3.5 mmol) was added by injection after 30 min. After a further 2 h at 0° C., the mixture was poured onto $H_2O$ (200 ml) and this mixture was extracted 3 times with ethyl acetate. The combined organic extracts were washed 3 times with $H_2O$, dried ($MgSO_4$) and concentrated. Chromatography on $SiO_2$ using E/H1/1 as eluent yielded the title compound.

$R_f(E/H\ 1/1) = 0.2\ MS(ESI) = 526(M + 1)$ f) 4-[3-(N-Glycyl-N-methylamino)benzyloxy]benzothiazole Hydrazine hydrate (0.3 ml) was added, at RT, to the title compound of Example 1e) (750 mg, 1.4 mmol) in ethanol (20 ml). After 1 h, the mixture was concentrated and dichloromethane (20 ml) was added. The resulting precipitate was filtered off with suction and the filtrate was concentrated, thereby yielding the title compound; the latter was used in the crude state for the next reaction step. MS(ESI)=396 (M+1)

g) 4-[3-(N-(3-Methoxycinnamoylglycyl)-N-methylamino)-2,6-dichlorobenzyloxy]benzothiazole Dicyclohexylcarbodiimide (DCC) (170 mg, 0.83 mmol) and hydroxybenzotriazole (HOBt) (150 mg, 1.13 mmol) were added, at RT, to 3-methoxycinnamic acid (130 mg, 0.75 mmol) in DMF (20 ml). The title compound of Example 1f) (300 mg, 0.75 mmol) in DMF (2 ml) was added after 30 min. After 18 h at RT, the mixture was diluted with ethyl acetate (100 ml) and washed, in each case twice, with 100 ml of saturated $Na_2CO_3$ solution, NaCl solution and $H_2O$; it was then dried ($MgSO_4$) and concentrated. Chromatography on $SiO_2$ using E/H 3/1 as eluent yielded the title compound of Example 1.

$R_f(E/H\ 1/1) = 0.2\ MS(FAB) = 556(M + 1)$

EXAMPLE 2

6-[3-(N-(3-Methoxycinnamoylglycyl)-N-methylamino)-2,6-dichlorobenzyloxy]benzothiazole The title compound was obtained in analogy with Example 1.

$R_f(E/H\ 1/1) = 0.2\ MS(FAB) = 556(M + 1)$

EXAMPLE 3

4-[3-(N-4-Trifluoromethylcinnamoylglycyl)-N-methylamino)-2,6-dichlorobenzyloxy]-2-methylbenzothiazole a) 2-Methoxyacetylaniline Acetyl chloride (9.6 g, 120 mmol) was added, at temperatures of between 0° C. and 10° C. and under argon, to 2-methoxyaniline (15 g, 120 mmol) and triethylamine (12.3 g, 120 mmol) in dichloromethane (100 ml). After 2 h, dichloromethane (100 ml) was added and the mixture was washed once (100 ml) on each occasion with saturated NaHCO$_3$ solution and 5% NaHSO$_4$ solution; it was then dried (CaCl$_2$) and concentrated, with the title compound resulting as an amorphous powder.

$R_f(E/H\ 1/1) = 0.2\ MS(ESI) = 166(M + 1)$ b) 2-Methoxythioacetylaniline

P$_2$S$_{10}$ (11.7 g, 53 mmol) was added to the title compound of Example 3a) (17.5 g, 106 mmol) in butyl acetate (100 ml), and the mixture was heated to boiling for 5 h. After it had been cooled down to RT, it was washed once on each occasion with H$_2$O (100 ml) and a saturated solution of NaHCO$_3$ (100 ml) and then once again with H$_2$O (100 ml); it was dried (MgSO$_4$) and concentrated, with the title compound resulting as an oil.

$R_f(E/H\ 1/1) = 0.35\ MS(ESI) = 182(M + 1)$ c) 4-Methoxy-2-methylbenzothiazole

A mixture of the title compound of Example 3b) (19 g, 105 mmol), 10% NaOH (300 ml) and ethanol (40 ml) was added slowly, at 80°–90° C., to a solution of potassium hexacyanoferrate (III) (138 g, 419 mmol) in H$_2$O (350 ml). After the addition had been completed, the temperature was maintained at 80°–90° C. for a further 4 h and the mixture was then allowed to cool to RT. It was then extracted 3 times with ethyl acetate (3×300 ml) and the combined organic extracts were dried (MgSO$_4$) and concentrated. Chromatography on SiO$_2$ using E/H 1/1 as eluent yielded the title compound as an amorphous powder.

$R_f(E/H\ 1/1) = 0.3\ MS(DCI) = 180(M + 1)$ d) 4-Hydroxy-2-methylbenzothiazole

The title compound of Example 3c) (16.4 g, 91.6 mmol), hydriodic acid (57% strength, 70 ml), acetic acid (15 ml) and red phosphorus (4.2 g) were boiled under reflux for 10 h. After the mixture had cooled down to RT, H$_2$O (200 ml) was added, the pH was adjusted to 5 with 2N NaOH, and the mixture was extracted 3 times with ethyl acetate (200 ml on each occasion). The combined organic extracts were dried (MgSO$_4$) and concentrated, with the title compound resulting as an amorphous powder.

$R_f(E/H\ 1/1) = 0.4\ MS(DCI) = 166(M + 1)$ e) trans-4-Trifluoromethylcinnamoyl chloride Thionyl chloride (335 μl, 4.6 mmol) was added, at 0° C., to 4-trifluoromethyl-E-cinnamic acid (1 g, 4.6 mmol) and pyridine (375 μl, 4.6 mmol) in dry CH$_2$Cl$_2$ (11 ml). The mixture was then stirred without cooling for 1 h, after which it was cooled down again to 0° C. and filtered while excluding moisture. The filtrate (10 ml) contained the title compound and was used in aliquots for the next reaction step.

f) 4-[3-(N-Glycyl-N-methylamino)-2,6-dichlorobenzyloxy]-2-methylbenzothiazole

The title compound was obtained in analogy with Example 1b)-f).

$R_f(\text{acetone}/H_2O\ 10/1) = 0.3\ MS(ESI) = 410(M + 1)$ g) 4-[3-(N-4-Trifluoromethylcinnamoylglycyl)-N-methylamino)-2,6-dichlorobenzyloxy]-2-methylbenzothiazole An aliquot of the solution of the title compound of Example 3e) (2 ml, 1.5 eq, 0.9 mmol) was added, at RT, to the title compound of 3f) (245 mg, 0.6 mmol) in dichloromethane (5 ml). After 18 h, saturated Na$_2$CO$_3$ solution (10 ml) was added and the whole was extracted 3 times with dichloromethane (3×20 ml). The organic phases were dried (CaCl$_2$) and concentrated. Chromatography on SiO$_2$ using ethyl acetate as eluent yielded the title compound of Example 3 as an amorphous powder.

$R_f(E) = 0.45\ MS(FAB) = 608(M + 1)$ h) Alternative synthesis of the title compound of Example 3

A mixture composed of the title compound of Example 3f) (200 mg, 0.49 mmol), 4-trifluoromethylcinnamic acid (106 mg, 0.49 mmol), O-[cyano(ethoxycarbonyl)methylenamino]-1,1,3,3-tetramethyluronium tetrafluoroborate (Totu) (160 mg, 0.49 mmol) and triethylamine (49 mg, 0.49 mmol) in NMP (10 ml) was stirred at RT for 1 h. The mixture was then diluted with ethyl acetate (100 ml), washed 2 times with saturated Na$_2$CO$_3$ and once with H$_2$O (100 ml on each occasion), dried (MgSO$_4$) and concentrated. Chromatography on SiO$_2$ using ethyl acetate as eluent yielded the title compound of Example 3.

Examples 6, 11, 12, 23, 37, and 39–41 were obtained in analogy with Examples 1 and 3. Examples 4, 5, 7, 8, 10, 13–22, and 24–36 may be obtained in analogy with Examples 1 and 3 (Tab. 1).

TABLE 1

| Example | R | R$^1$ | MS (M + 1) |
|---|---|---|---|
| 4 | (cinnamoyl-4-NH$_2$-phenyl) | CH$_3$ | |
| 5 | (cinnamoyl-4-N(CH$_3$)-phenyl) | CH$_3$ | |
| 6 | (pentadienoyl) | CH$_3$ | 490 |
| 7 | (alkyl-branched acyl) | CH$_3$ | |

TABLE 1-continued
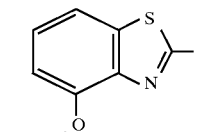
| Example | R | R¹ | MS (M + 1) |
|---|---|---|---|
| 8 | 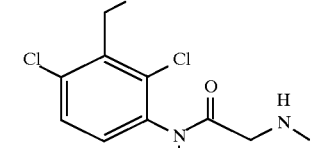 | CH₃ | |
| 10 | 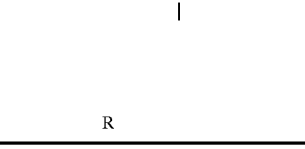 | CH₃ | |
| 11 | 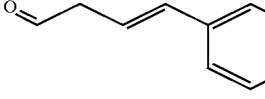 | CH₃ | 570 |
| 12 | 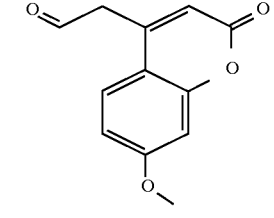 | CH₃ | 530 |
| 13 | 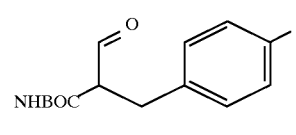 | CH₃ | |
| 14 | 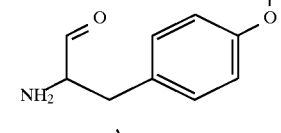 | CH₃ | |
| 15 | 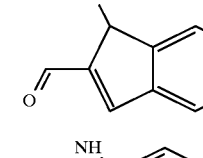 | CH₃ | |
| 16 | 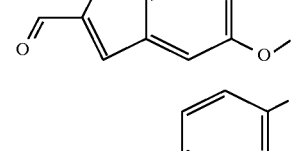 | CH₃ | |
| 17 | 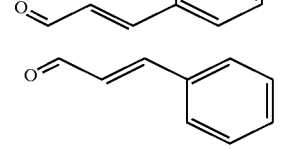 | CH₃ | |
| 18 | 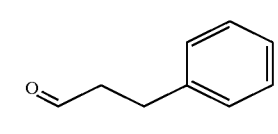 | CH₃ | |
| 19 |  | CH₃ | |
| 20 |  | CH₃ | |
| 21 |  | CH₃ | |
| 22 |  | CH₃ | |
| 23 |  | CH₃ | 554 |
| 24 |  | CH₃ | |
| 25 |  | CH₃ | |

TABLE 1-continued

| Example | R | R¹ | MS (M + 1) |
|---|---|---|---|
| 26 | cyclopropyl-phenyl aldehyde | CH₃ | |
| 27 | 2,4-dimethoxyphenyl propenal | CH₃ | |
| 28 | 4,5-dimethoxy-2-nitrophenyl propenal | CH₃ | |
| 29 | 2,4,5-trimethoxyphenyl propenal | CH₃ | |
| 30 | 2,3-dimethoxyphenyl propenal | CH₃ | |
| 31 | phenylthio acetaldehyde | CH₃ | |
| 32 | phenoxy acetaldehyde | CH₃ | |
| 33 | (2,4-dichloro-5-methylphenylthio)acetaldehyde | CH₃ | |
| 34 | (4-methoxyphenoxy)acetaldehyde | CH₃ | |
| 35 | (3-methoxyphenoxy)acetaldehyde | CH₃ | |
| 36 | (4-fluorophenoxy)acetaldehyde | CH₃ | |
| 37 | (4-trifluoromethoxyphenoxy)acetaldehyde | CH₃ | 628 |
| 39 | (3-methoxyphenyl)propenal | phenyl | 632 |
| 40 | (4-trifluoromethylphenyl)propenal | phenyl | 670 |
| 41 | (4-methylphenyl)propenal | phenyl | 616 |

EXAMPLE 42

4-[3-(N-4-Methoxybenzylureidoacetyl)-N-methylamino)-2,6-dichlorobenzyloxy]-2-methylbenzothiazole The title compound of Example 3f (200 mg, 0.49 mmol), diisopropylethylamine (63 mg, 0.49 mmol) and N,N-carbonyldiimidazole (80 mg, 0.49 mmol) in NMP (10 ml)

were stirred at RT for 4 h. 4-Methoxybenzylamine (60 mg, 0.49 mmol) was then added. After a further 18 h, ethyl acetate (100 ml) was added and the mixture was washed once on each occasion with 50 ml each of saturated $Na_2CO_3$ solution, 5% $NaHSO_4$ solution and $H_2O$, and then dried ($MgSO_4$) and concentrated. Chromatography on $SiO_2$ using ethyl acetate as eluent yielded the title compound as an amorphous powder.

$R_f(E) = 0.15$ $MS(FAB) = 573(M + 1)$

The compounds of Examples 43 and 44 were obtained in analogy with Example 42.

TABLE 2

| Example | R' | R | MS (M + 1) |
|---|---|---|---|
| 43 | CH₃ | (structure with CO₂, NH, benzyl) | 614 |
| 44 | CH₃ | (structure with CO₂, NH, 4-hydroxybenzyl) | 645 |

EXAMPLE 45

4-[3-Benzyloxycarbonylaminoacetyl-N-methylamino)-2,6-dichlorobenzyloxy]-2-methylthiazole a) N-benzyloxycarbonylsuccinimide (112 mg, 0.49 mmol) was added, at RT, to the pound of Example 3f) (200 mg, 0.49 mmol) and diisopropylethylamine (63 mg, 0.49 mmol) in NMP (1 0 ml). After 18 h, the mixture was poured onto $H_2O$ (50 ml) and the whole was extracted 3 times with ethyl acetate (50 ml on each occasion). The combined organic extracts were dried ($MgSO_4$) and concentrated. Chromatography on $SiO_2$ using ethyl acetate as solvent yielded the title compound of Example 45 as an amorphous powder.

$R_f(E) = 0.5$ $MS(FAB) = 544(M + 1)$ b) Alternative synthesis of the title compound of Example 45

Benzyl alcohol (52 mg, 0.49 mmol), diisopropylethylamine (63 mg, 0.49 mmol), N,N-carbodiimidazole (80 mg, 0.49 mmol) and a spatula tip of DMAP were stirred at RT for 8 h. The title compound of Example 3f) (200 mg, 0.49 mmol) was then added. After 18 h, the mixture was poured onto $H_2O$ (50 ml) and the whole was extracted 3 times with ethyl acetate (50 ml on each occasion). The combined organic extracts were dried ($MgSO_4$) and concentrated. Chromatography on $SiO_2$ using ethyl acetate as eluent yielded the title compound of Example 45.

EXAMPLE 46

4-[3-N(4-Trans-trifluoromethylcinnamoylglycyl)-N-methylamino)-6-chloro-2-methoxybenzyloxy]-2-methylbenzothiazole a) 2-Chloro-6-methoxy-3-nitrotoluene, 6-chloro-2-methoxy-3-nitrotoluene, and 2,6-dimethoxy-3-nitrotoluene Methanol (5.8 ml, 0.145 mol) was added, at 0° C., to sodium hydride (5.8 g of a 60% suspension in mineral oil) in DMF (200 ml). After 30 min, 2,6-dichloro-3-nitrotoluene (30 g, 0.145 mol) in DMF was added by injection, in association with which the temperature rose to ~20° C. The mixture was subsequently stirred for 1.5 h without cooling and then added to ice (~300 g); the whole was then extracted 3 times with ethyl acetate (3×800 ml). The extracts were dried ($MgSO_4$) and concentrated in vacuo.

Chromatography on $SiO_2$ using E/H 1/2 as eluent yields the three title compounds as oils.

1. (2-methoxy-6-chloro) isomer Rf (E/H 1/2)=0.4
2,6-dimethoxy-3-nitrotoluene Rf (E/H 1/2)=0.3
2. (2-chloro-6-methoxy) isomer Rf (E/H 1/2)=0.25
MS (DCI)=202 (M+1) for the two chloro, methoxy isomers
MS (DCI)=198 (M+1) for the dimethoxy product b) 2-Methoxy-6-chloro-3-nitrobenzyl bromide 1. The isomer from the title compound of Example 46a (8 g, 40 mmol) was reacted in analogy with the title compound of Example 1a).

$R_f(E/H\ 1/2) = 0.35$ $MS(DCI) = 280(M + 1)$ c) The title compound of Example 46 was obtained in analogy with Examples 1 and 3.

$R_f(E) = 0.4$ $MS(FAB) = 604(M + 1)$

The compounds of Examples 47 and 48 may be obtained in analogy with Example 46.

TABLE 3

| Example | R¹ | R² | R³ | MS (M + 1) |
|---|---|---|---|---|
| 47 | Cl | | OMe | 4-CF₃ |
| 48 | OMe | OMe | 4-CF₃ | |

What is claim is:

1. A compound of the formula (I)

in which the symbols have the following meanings:
a) $X_1$ is N;
one of the radicals $X_2$ or $X_3$ is C—O—$R^2$, and the other, $X_2$ or $X_3$, in each case, and $X_4$, are $CR^1$;

b) $R^1$ and $R^3$ are, identically or differently,
  (1) H
  (2) halogen
  (3) $(C_1-C_6)$-alkyl
  (4) O—$R^6$
  (5) S—$R^6$
  (6) $NHR^6$
  (7) $(C_6-C_{12})$-aryl
  (8) $(C_6-C_{12})$-aryl-$(C_1-C_3)$-alkyl
  (9) $C(O)$—$OR^6$
  (10) $C(O)$—H
  (11) $(C_2-C_5)$-alkenyl
  (12) $NO_2$
  (13) $SO_3R^7$
  (14) CN
  (15) $C(O)$—$NHR^8$
  where (3), (7), (8) and (11) can optionally be substituted by one or more substituents selected from $C(O)—(O)_O—(C_1-C_5)$-alkyl, $OR^6$, $SR^7$, $NO_2$, CN, $NHR^8$ and halogen;

c) $R^2$ is a radical of the formula (II)

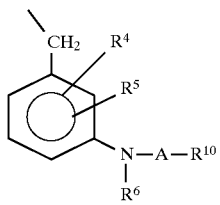

(II)

d) $R^4$ and $R^5$ are, identically or differently,
  (1) H
  (2) halogen
  (3) $OR^6$
  (4) $SR^6$
  (5) CN
  (6) $(C_1-C_5)$-alkyl;

e) $R^6$, $R^7$ and $R^8$ are, identically or differently,
  (1) H
  (2) $(C_1-C_5)$-alkyl
  (3) $(C_3-C_5)$-alkenyl
  (4) $(C_6-C_{12})$-aryl-$(C_1-C_3)$-alkyl;
  (5) $(C_3-C_{10})$-cycloalkyl,
  (6) $(C_3-C_{10})$-cycloalkyl-$(C_1-C_3)$-alkyl;
  (7) $C(O)—(O)_O—(C_1-C_5)$-alkyl,
  (8) $C(O)—(NH)_O—(C_1-C_5)$-alkyl;

f) A is an aminocarboxylic acid selected from methionine, alanine, phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, O-methyltyrosine, β-(2-thienyl)alanine, glycine, cyclohexylalanine, leucine, isoleucine, valine, norleucine, phenylglycine, serine, cysteine, aminopropionic acid and aminobutyric acid;

g) $R^9$ is
  (1) H
  (2) $C(O)—(O)_O—(C_1-C_5)$-alkyl
  (3) $C(O)—(O)_O—(C_1-C_3)$-alkyl-$(C_6-C_{10})$aryl;

h) $R^{10}$ is
  (1)—$C(O)$—D–E
  (2)—$C(S)$—D–E
  (3)—$SO_2$—D–E
  (4) hydrogen;

i) D is
  (1) $(C_2-C_5)$-alkenediyl
  (2) $(C_1-C_8)$-alkanediyl
  (3)—$(CH_2)_n$—$Y_o$—$(CH_2)_m$—
  (4) $(C_3-C_{10})$-cycloalkanediyl
  (5) $(C_3-C_{10})$-cycloalkyl-$(C_1-C_3)$-alkanediyl
  (6) $(C_3-C_{10})$-cycloalkenediyl
  (7) $(C_3-C_{10})$-cycloalkenyl-$(C_1-C_3)$-alkanediyl
  where (1)–(7) can optionally be substituted by one or more substituents selected from $OR^6$, $NO_2$, CN, $CO_2R^7$, $NR^8R^9$, $SO_2R^6$, $SO_2NR^8R^9$, $SO_3R^7$ or $C(O)—NR^8R^9$;

j) E is
  (1) H
  (2) $(C_6-C_{10})$-aryl,
  (3) $(C_1-C_9)$-heteroaryl,
  where (2) and (3) can optionally be substituted by one or more substituents selected from $NR^8R^9$, CN, $CO_2R^6$, $SO_3R^7$, $NO_2$, $SO_2NR^8R^9$, $SO_2R^6$, O—$(C_1-C_5)$-alkyl, S—$(C_1-C_5)$-alkyl, $(C_1-C_5)$-alkyl and $(C_2-C_5)$-alkenyl, where O—$(C_1-C_5)$-alkyl and $(C_1-C_5)$-alkyl can optionally be partially or completely substituted by halogen;

k) Y is
  (1) O
  (2) S
  (3) $NR^8$;

l) n and m are, identically or differently, a number 0–6;
m) o is 0 or 1;
or a physiologically tolerated salt thereof.

2. A compound of the formula (I) as claimed in claim 1, in which:
a) $R^1$ and $R^3$ are, identically or differently,
  (1) H
  (2) $(C_1-C_6)$-alkyl
  (3) O—$R^6$
  (4) S—$R^6$
  (5) $NHR^6$
  (6) $(C_2-C_5)$-alkenyl
  (7) $C(O)$—$OR^6$
  (8) $C(O)$—H
  (9) $NO_2$
  (10) CN
  (11) $C(O)$—$NHR^8$
  where (2) and (6) can optionally be substituted by one or more substituents selected from halogen, $CO_2R^6$, or $NHR^8$;

b) $R^6$, $R^7$ and $R^8$ are, identically or differently,
  (1) H
  (2) $(C_1-C_5)$-alkyl
  (3) $(C_6-C_{10})$-aryl-$(C_{1-C3})$-alkyl;
  or a physiologically tolerated salt thereof.

3. A compound of the formula (I) as claimed in claim 1 or 2, in which:
a) $R^1$ and $R^3$ are, identically or differently,
  (1) H
  (2) $(C_1-C_4)$-alkyl
  (3) NH—$(C_1-C_5)$alkyl
  (4) O—$(C_1-C_5)$alkyl
  (5) S—$(C_1-C_5)$-alkyl
  (6) $C(O)$—H
  (7) $CO_2R^6$
  (8) $(C_2-C_3)$-alkenyl
  where (2)–(5) and (8) can be substituted by one or more substituents selected from halogen, $CO_2R^6$ or $NHR^8R$;

b) A is selected from leucine, isoleucine, valine, alanine, methionine, glycine, serine, aminopropionic acid and aminobutyric acid; or a physiologically tolerated salt thereof.

4. A compound of the formula (I) as claimed in claim 1 wherein the compound is 4-[3-(N-(3-Methoxycinnamoylglycyl)-N-methylamino)-2,6-dichlorobenzyloxy]benzothiazole or a physiologically tolerated salt thereof.

5. A compound of the formula (I) as claimed in claim 1 wherein the compound is 6-[3-(N-(3-Methoxycinnamoylglycyl)-N-methylamino)-2,6-dichlorobenzyloxy]benzothiazole or a physiologically tolerated salt thereof.

6. A compound of the formula (I) as claimed in claim 1 wherein the compound is 4-[3-(N-(4-Trifluoromethylcinnamoylglycyl)-N-methylamino)-2,6-dichlorobenzyloxy]-2methylbenzothiazole or a physiologically tolerated salt thereof.

7. A compound of the formula (I) as claimed in claim 1 wherein the compound is 4-[3-(N-Pent-2,4-dienoylglycyl)-N-methylamino)-2,6-dichlorobenzyloxy]-2-methylbenzothiazole or a physiologically tolerated salt thereof.

8. A compound of the formula (I) as claimed in claim 1 wherein the compound is 4-[3-(N-(3-Methoxycinnamoylglycyl)-N-methylamino)-2,6-dichlorobenzyloxy]-2-methylbenzothiazole or a physiologically tolerated salt thereof.

9. A compound of the formula (I) as claimed in claim 1 wherein the compound is 4-[3-(N-(3-(Fur-2-yl)prop-2-enoylglycyl)-N-methylamino)-2,6-dichlorobenzyloxy]-2-methylbenzothiazole or a physiologically tolerated salt thereof.

10. A compound of the formula (1) as claimed in claim 1 wherein the compound is 4-[3-(N-(4-Methylcinnamoylglycyl)-N-methylamino)-2,6-dichlorobenzyloxy]-2-methylbenzothiazole or a physiologically tolerated salt thereof.

11. A compound of the formula (I) as claimed in claim 1 wherein the compound is 4-[3-(N-(3-Methoxycinnamoylglycyl)-N-methylamino)-2,6-dichlorobenzyloxy]-2-phenylbenzothiazole or a physiologically tolerated salt thereof.

12. A compound of the formula (I) as claimed in claim 1 wherein the compound is 4-[3-(N-((4-Trifluoromethoxyphenoxy)acetylglycyl)-N-methylamino)-2,6-dichlorobenzyloxy]-2-methylbenzothiazole or a physiologically tolerated salt thereof.

13. A compound of the formula (I) as claimed in claim 1 wherein the compound is 4-[3-(N-(4-Trifluoromethylcinnamoylglycyl)-N-methylamino)-2,6-dichlorobenzyloxy]-2-phenylbenzothiazole or a physiologically tolerated salt thereof.

14. A compound of the formula (I) as claimed in claim 1 wherein the compound is 4-[3-(N-(4-Methylcinnamoylglycyl)-N-methylamino)-2,6-dichlorobenzyloxy]-2-phenylbenzothiazole or a physiologically tolerated salt thereof.

15. A compound of the formula (I) as claimed in claim 1 wherein the compound is 4-[3-(N-(4-Methoxybenzylureidoacetyl)-N-methylamino)-2,6-dichlorobenzyloxy]-2-methylbenzothiazole or a physiologically tolerated salt thereof.

16. A compound of the formula (I) as claimed in claim 1 wherein the compound is 4-[3-(N-(1 –Carbomethoxy-2-phenylethyl)ureidoacetyl)-N-methylamino)-2,6-dichlorobenzyloxy]-2-methylbenzothiazole or a physiologically tolerated salt thereof.

17. A compound of the formula (I) as claimed in claim 1 wherein the compound is 4-[3-(N-(1 –Carboethoxy-2-(4-hydroxyphenyl)ethyl)ureidoacetyl)-N-methylamino)-2,6-dichlorobenzyloxy]-2-methylbenzothiazole or a physiologically tolerated salt thereof.

18. A compound of the formula (I) as claimed in claim 1 wherein the compound is 4-[3-(N-Benzyloxycarbonylaminoacetyl-N-methylamino)-2,6-dichlorobenzyloxy]-2-methylbenzothiazole or a physiologically tolerated salt thereof.

19. A compound of the formula (I) as claimed in claim 1 wherein the compound is 4-[3-N-(4-Trans-trifluoromethylcinnamoylglycyl)-N-methylamino)-6-chloro-2-methoxybenzyloxy]-2-methylbenzothiazole or a physiologically tolerated salt thereof.

20. A pharmaceutical composition comprising an effective quantity of a compound of the formula (I) as claimed in claim 1 or a physiologically tolerated salt thereof.

21. The method of treating pain comprising administering an effective quantity of a compound of the formula (I) as claimed in claim 1 or a physioglically tolerated salt thereof.

22. The method of treating asthma comprising administering an effective quantity of a compound of the formula (I) as claimed in claim 1 or a physiologically tolerated salt thereof.

* * * * *